US00PP19925P2

(12) United States Plant Patent
Zaiger et al.

(10) Patent No.: US PP19,925 P2
(45) Date of Patent: Apr. 14, 2009

(54) **INTERSPECIFIC *PRUNUS* TREE NAMED 'BELLA ROYALE'**

(50) Latin Name: ***Prunus* species**
Varietal Denomination: Bella Royale

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 0 days.

(21) Appl. No.: 12/079,584

(22) Filed: Mar. 28, 2008

(51) Int. Cl.
*A01H 5/00* (2006.01)

(52) U.S. Cl. ..... Plt./180

(58) Field of Classification Search ..... Plt./180
See application file for complete search history.

*Primary Examiner*—Annette H Para

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consists of the following combination of desirable features.

1. Heavy and regular production of fruit.
2. Fruit with very good flavor and eating quality.
3. Fruit maturing in the late maturity season.
4. Vigorous, upright tree growth.
5. Fruit with an attractive orange red skin color.
6. Fruit with an average Brix of 20.1°, with a good balance between acid and sugar.

1 Drawing Sheet

Botanical classification: *Prunus* species.

BACKGROUND OF THE VARIETY

Field of the Invention

In the field of plant genetics, we conduct an extensive and continuing plant-breeding program, including the organization and asexual reproduction of orchard trees, and of which plums, peaches, nectarines, apricots, almonds, cherries and interspecifics are exemplary. It was against this background of our activities that the present variety of interspecific tree was originated and asexually reproduced by us in our experimental orchard located near Modesto, Stanislaus County, Calif.

PRIOR VARIETIES

Among the existing varieties of plum and interspecific trees, which are known to us, and mentioned herein, are the proprietary interspecific tree developed in our program with identification numbers 75Z655, the plum trees 'Friar' (non-patented), 'Mariposa' (U.S. Plant Pat. No. 111), 'Casselman' (non-patented), 'Amazon' Plum (U.S. Plant Pat. No. 2,043), the Interspecific 'Flavorosa' (U.S. Plant Pat. No. 10,285), and the proprietary plumcot '4G1180'.

STATEMENT REGARDING FEDERALLY SPONSORED RESEARCH AND DEVELOPMENT: Not applicable.

ORIGIN OF THE VARIETY:

The new and distinct variety of interspecific tree, was originated by us from multiple crosses of the following species, [*Prunus salicina*×(*Prunus salicina*×*Prunus armeniaca*)] in our experimental orchard located near Modesto, Calif. as a selected seedling from open pollinated seed of our interspecific proprietary seedling with field identification number '75Z655' (the pollen parent is unknown). The variety of interspecific tree with identification number '75Z655' was developed by us from multiple crosses between the following plum trees 'Friar' (non-patented), 'Mariposa' (U.S. Plant Pat. No. 111), 'Casselman' (non-patented), 'Amazon' Plum (U.S. Plant Pat. No. 2,043), the Interspecific 'Flavorosa' (U.S. Plant Pat. No. 10,285) and the proprietary plumcot with identification number '4G1180'. A large number of these open pollinated seedlings, growing on their own root system, were budded to older trees of 'Nemaguard' Rootstock (non-patented) to induce earlier maturity and fruit evaluation, under close and careful observation the present seedling exhibited desirable tree and fruit characteristics, was selected in 2003 for additional asexual propagation and commercialization.

ASEXUAL REPRODUCTION OF THE VARIETY:

Additional asexual reproduction of the new and distinct variety of interspecific tree was by budding to 'Nemaguard' Rootstock (non-patented), as performed by us in our experimental orchard located near Modesto, Calif. and shows that reproductions run true to the original tree and all characteristics of the tree and its fruit are established and transmitted through succeeding asexual propagations.

SUMMARY OF THE NEW INTERSPECIFIC TREE:

The new variety of interspecific tree is of large size, vigorous upright growth and a productive and regular bearer of medium size, orange flesh fruit with very good flavor and eating quality. The fruit is further characterized by being nearly globose in shape, holding firm on the tree 7 to 10 days after maturity (firm ripe) and the flesh having a good balance between acid and sugar with an average of 20.1° Brix. In comparison to its seed parent '75Z655' it is larger in size and approximately 30 days later in maturity. In comparison to the plum parents used in the genetic make up of '75Z655', 'Friar' (non-patented), 'Mariposa' (U.S. Plant Pat. No. 111), 'Casselman' (non-patented), 'Amazon' (U.S. Plant Pat. No. 2,043) and the Interspecific 'Flavorosa' (U.S. Plant Pat. No. 10,285) all have smooth slick skin surfaces compared to the pubescent skin surface of the new variety, which is similar to plumcots and apricots.

PHOTOGRAPHS OF THE VARIETY

The accompanying color photographic illustration shows typical specimens of the foliage and fruit of the present new interspecific variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 6 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 6 year old specimens grown near Modesto, Calif., with color in accordance with Munsell Book of Color.

Tree:

*Size.*—Large, pruned to 3 to 3.5 meters in height for economical harvesting of fruit. Average width of 3 meters, varies with different cultural practices.

*Vigor.*—Vigorous, tree growth of approximately 1.5 to 2 meters the first growing season, varies with cultural practices, soil type, fertility and climatic conditions.

*Form.*—Upright, usually pruned to vase shape.

*Branching habit.*—Upright, crotch angle approximately 30°, increases with heavy crop load.

*Productivity.*—Productive, thinning and spacing of fruit necessary for desired market size.

*Bearer.*—Regular, adequate fruit set 4 consecutive years. No alternate bearing observed.

*Fertility.*—Self sterile, pollinator required.

*Density.*—Medium dense, usually pruned to vase shape to increase sunlight to center of tree to enhance fruit color and health of fruit spurs.

*Hardiness.*—Hardy in all stone fruit growing areas of California. Tree grown in USDA Hardiness Zone 9. Winter chilling requirement approximately 800 hours at or below 45° F.

TRUNK:

*Size.*—Medium, 45.5 cm at 28 cm above ground level on 6 year old trees.

*Stocky.*—Medium.

*Texture.*—Medium shaggy, roughness increases with age.

*Color.*—Varies from 10YR 2/2 to 10YR 4/2.

Branches:

*Size.*—Medium. Average circumference 14.7 cm at 1.2 meters above ground on a 6 year old tree. Crotch angle approximately 30°, increase with heavy crop load.

*Surface texture.*—New growth relatively smooth. Mature growth medium rough, roughness increases with age.

*Lenticels.*—Size — medium. Average length 3.7 mm. Average width 1.4 mm. Average number 27 in a 25.8 sq cm surface of branch. Color varies from 2.5Y 6/8 to 2.5Y 6/10.

*Color.*—New growth varies from 2.5GY 5/6 to 5GY 6/6. Old growth varies from 10YR 3/4 to 7.5YR 3/6, varies with age of growth.

Leaves:

*Size.*—Small to medium. Average length 89.1 mm. Average width 37.1 mm.

*Form.*—Oblanceolate.

*Apex.*—Acuminate.

*Base.*—Cuneate.

*Margin.*—Serrulate.

*Thickness.*—Medium.

*Surface texture.*—Upper surface relatively smooth, slightly indented over midrib and leaf veins, glabrous. Lower surface relatively smooth, small ridges created by midrib and pinnate venation, glabrous.

*Petiole.*—Average length 14.6 mm. Average width 1.4 mm. Longitudinally grooved. Surface — light pubescence. Color varies from 5GY 7/6 to 5GY 6/6.

*Glands.*—Type — globose. Size — medium. Average length 1.2 mm. Average diameter 0.5 mm. Number varies from 2 to 3, average number 2. Located on base of leaf blade and upper portion of petiole. Color varies from 5Y 6/6 to 5GY 5/6.

*Color.*—Upper surface varies from 5GY 4/4 to 5GY 4/6. Lower surface varies from 5GY 5/4 to 5GY 5/6. Midrib color varies from 2.5GY 7/4 to 2.5GY 8/4.

Flower buds:

*Size.*—Medium. Average length 9.5 mm. Average diameter 4.9 mm.

*Hardiness.*—Hardy with respect to California winters.

*Form.*—Conical, becomes elongated just before opening.

*Pedicel.*—Length — medium. Average length 11.4 mm. Average width 0.7 mm. Color varies from 2.5GY 7/8 to 5GY 7/6.

*Color.*—N 9.5/ (white).

*Number of buds per spur.*—Average number 7, varies from 5 to 10. Varies with age of spur.

Flowers:

*Blooming period.*—Date of First Bloom Mar. 2, 2007. Date of Petal Fall Mar. 11, 2007, varies slightly with climatic conditions.

*Size.*—Medium. Average height 9.7 mm. Average diameter 17.3 mm.

*Petals.*—Size — small to medium. Number — normally 5, alternately arranged to sepals. Average length 8.9 mm. Average width 7.5 mm. Form — elliptical. Margin — sinuate. Color — N 9.5/ (white). Both surfaces glabrous.

*Sepals.*—Number — normally 5, alternately arranged to petals. Size — small. Average length 2.5 mm. Average width 2.3 mm. Form — ovate, apex rounded. Margin — entire. Color — upper surface varies from 5GY 6/6 to 5GY 6/8. Lower surface varies from 2.5GY 6/6 to 5GY 6/8. Both surfaces glabrous.

*Stamen.*—Average number per flower 33. Average filament length 6.8 mm. Filament color N 9.5/ (white). Anther color varies from 5Y 8/6 to 5Y 8/8.

*Pollen.*—Self sterile, pollinator required. Color varies from 5Y 8/10 to 5Y 7/10.

*Pistil.*—Normally one. Surface pubescent. Average length 7.7 mm. Stigma height approximately 0.7 mm below anthers. Color varies from 10Y 7/6 to 2.5GY 8/6.

*Fragrance.*—Moderate to heavy aroma.

*Color.*—N 9.5/ (white).

*Number flowers per flower bud.*—Average number 3, varies from 1 to 4.

*Pedicel.*—Average length 12.8 mm. Average width 0.8 mm. Color varies from 2.5GY 6/8 to 5GY 7/8. Surface — glabrous.

Fruit:

*Maturity when described.*—Firm ripe.

*Date of first picking.*—Aug. 1, 2007.

*Date of last picking.*—Aug. 9, 2007, varies slightly with climatic conditions.

*Size.*—Medium. Average diameter axially 56.9 mm. Average transversely in suture plane 56.1 mm. Average weight 122.1 grams, varies slightly with fertility of the soil, amount of thinning and climatic conditions.

*Form.*—Globose.

*Suture.*—Nearly smooth, extends from base to apex.

*Ventral surface.*—Nearly smooth.

*Apex.*—Rounded, some fruit with very slight tip.

*Base.*—Varies from flat to slightly retuse.

Stem:

*Size.*—Medium. Average length 16.7 mm. Average diameter 2.4 mm.

*Cavity.*—Rounded to slightly elongated in suture plane. Average depth 2.4 mm. Average diameter 4.7 mm.

*Color.*—Varies from 10YR 4/6 to 7.5Y 7/8, varies with exposure to sunlight.

Flesh:

*Ripens.*—Evenly, slightly earlier near skin surface.

*Texture.*—Firm, smooth, uniform.

*Fibers.*—Few, small, tender.

*Firmness.*—Firm, similar to firmness of 'Mariposa' Plum (U.S. Plant Pat. No. 111).

*Aroma.*—Slight to moderate.

*Amydgalin.*—Undetected.

*Eating quality.*—Very good.

*Flavor.*—Very good, good balance between acid and sugar.

*Juice.*—Moderate to heavy, enhances flavor.

*Brix.*—Average 20.1° varies slightly with amount of fruit per tree and climatic conditions.

*Color.*—Varies from 7.5YR-6/12 to 10R 6/12 next to skin. Stone cavity non-bleeding, varies from 2.5YR 6/8 to 2.5YR 5/8.

*Stone cavity.*—Shape — ovoid. Average length 26.9 mm. Average width 20.5 mm. Average depth 5.3 mm.

Skin:

*Thickness.*—Medium.

*Surface.*—Nearly smooth.

*Pubescence.*—Moderate amount, very short.

*Tendency to crack.*—None.

*Color.*—Ground color varies from 5GY 9/4 to 5Y 8/6. Overspread with 7.5R 3/6 to 7.5R 3/8.

*Tenacity.*—Tenacious to flesh.

*Astringency.*—None.

Stone:

*Type.*—Clingstone.

*Size.*—Medium. Average length 24.9 mm. Average width 18.6 mm. Average thickness 10.5 mm.

*Form.*—Ovoid.

*Base.*—Relatively flat, varies from flat to slightly rounded.

*Apex.*—Slightly pointed. Average length 1.6 mm.

*Surface.*—Slightly pitted throughout. A small narrow groove on each side of suture plane.

*Sides.*—Unequal, one side extending slightly further from suture plane.

*Ridges.*—Small narrow ridge on each side of suture extending from base toward apex.

*Tendency to split.*—None.

*Color.*— 5YR 5/8.

Kernel:

*Size.*—Small to medium. Average length 14.9 mm. Average width 10.1 mm. Average depth 5.6 mm.

*Form.*—Ovoid.

*Skin color.*— 2.5Y 7/6.

*Viability.*—Viable, complete embryo development.

Use: Dessert.

*Market.*—Local and long distance.

Keeping quality: Good, held firm in cold storage 2 weeks at 38° to 42° without shriveling, internal breakdown of flesh or appreciable loss of eating quality.

Shipping quality: Good, showed minimal skin scarring or bruising during picking, packing or shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

What is claimed is:

1. A new and distinct variety of interspecific tree, substantially as illustrated and described, characterized by its large size, upright growth and being a productive and regular bearer of medium size, clingstone fruit with very good flavor and eating quality. The fruit is further characterized by having good shipping and storage quality and in comparison to the proprietary seed parent '75Z655' the new variety is larger in size and approximately 30 days later in maturity.

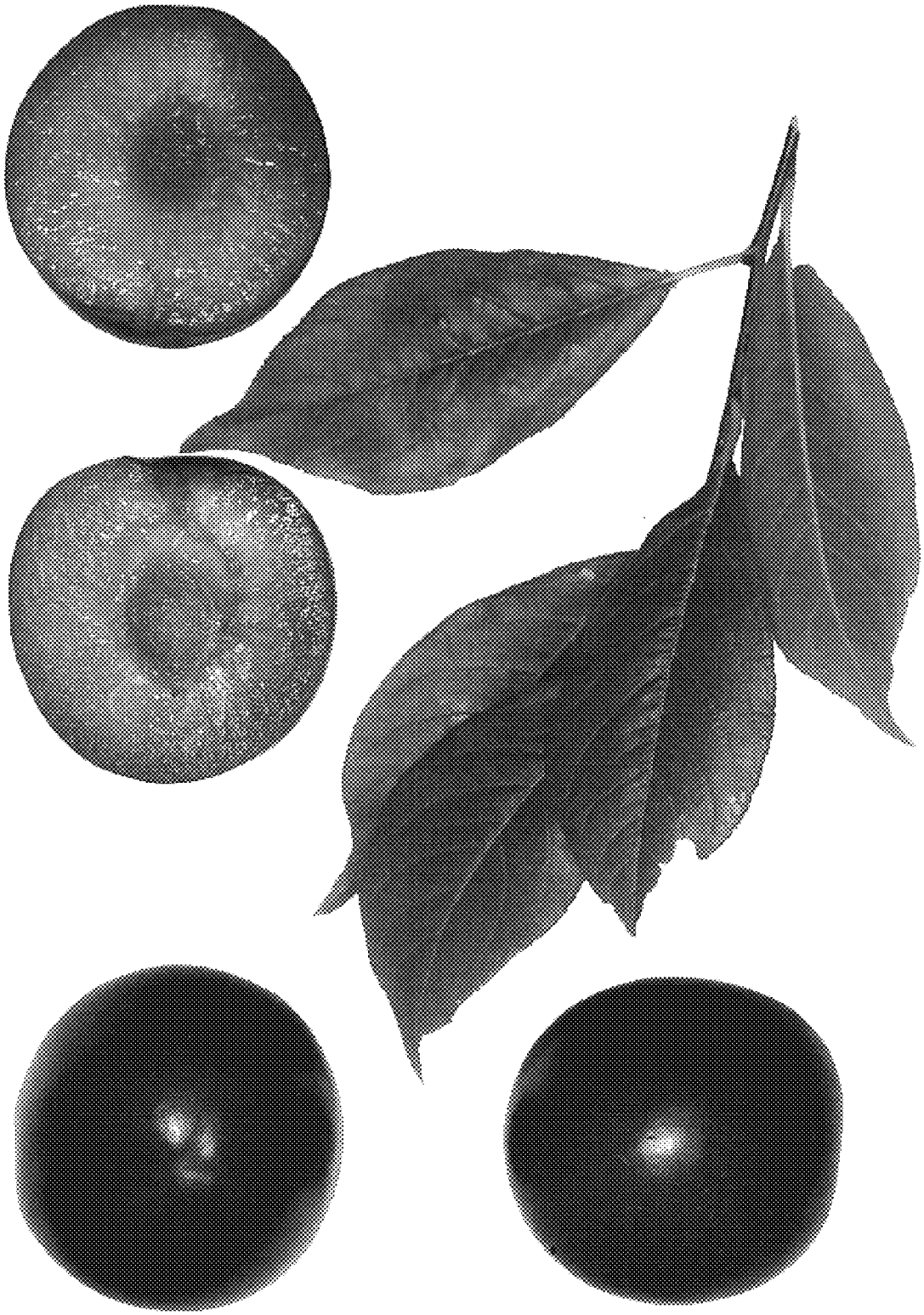

* * * * *